United States Patent [19]

Lacey

[11] Patent Number: 4,807,148

[45] Date of Patent: Feb. 21, 1989

[54] DECONVOLVING CHROMATOGRAPHIC PEAKS

[75] Inventor: Richard F. Lacey, Palo Alto, Calif.

[73] Assignee: Hewlett-Packard Company, Palo Alto, Calif.

[21] Appl. No.: 57,077

[22] Filed: May 29, 1987

[51] Int. Cl.⁴ ............................................. G01N 31/08
[52] U.S. Cl. .................................... 364/498; 364/497; 364/577; 73/23.1; 73/61.1 C
[58] Field of Search ............... 364/497, 498, 577, 723, 364/725; 73/23.1, 61.1 C

[56]  References Cited

U.S. PATENT DOCUMENTS

| | | | |
|---|---|---|---|
| 4,180,857 | 12/1979 | Yoshihara et al. | 364/497 |
| 4,314,343 | 2/1982 | Tomlinson | 364/498 |
| 4,353,242 | 10/1982 | Harris et al. | 73/23.1 |
| 4,374,424 | 2/1983 | Coustre et al. | 364/497 |
| 4,642,778 | 2/1987 | Hieftje et al. | 364/498 |

Primary Examiner—Parshotam S. Lall
Assistant Examiner—Ellis B. Ramirez
Attorney, Agent, or Firm—John A. Frazzini

[57]  ABSTRACT

Deconvolution of up to three overlapping chromatographic peaks is provided in which pure spectral components are extrapolated from a Euclidean-normalized expression of chromatographic data in the space of the three principal factors. A coordinate transformation to planar coordinates after expansion in factor space and before extrapolation yields the simplicity of linear extrapolation in combination with the inherent accuracy of Euclidean, as opposed to standard, normalization. The estimation of the pure component spectra permits the constructions of a concentration matrix. Improved estimates and an error bound are provided by applying assumptions of non-negativity and limited deviation from the means to the concentration matrix.

13 Claims, 5 Drawing Sheets

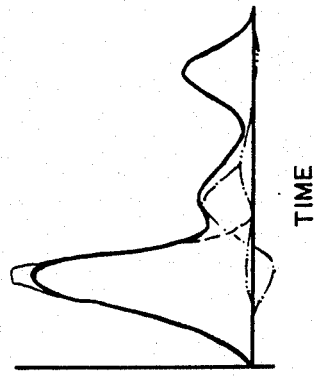
FIG. 9
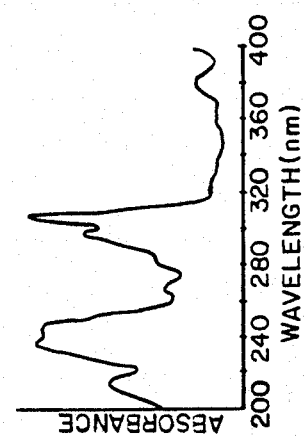
FIG. 6b
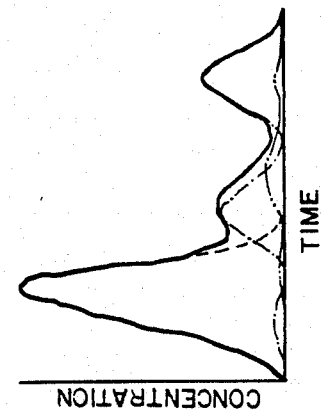
FIG. 10
Change in Peak Areas and Error Bound with
Iteration of Routine To Improve Spectral Estimates
| iteration | area of peak | | | | error bound |
|---|---|---|---|---|---|
| | 1 | 2 | 3 | 4 | |
| 1 | 167.2 | 17.8 | 7.7 | 41.1 | 77.0 |
| 2 | 155.0 | 31.2 | 9.4 | 39.5 | 20.2 |
| 3 | 153.4 | 33.3 | 9.3 | 39.1 | 15.2 |
| 4 | 152.5 | 34.4 | 9.3 | 38.8 | 11.7 |
| 5 | 151.9 | 35.3 | 9.3 | 38.6 | 10.1 |
FIG. 9

DECONVOLVING CHROMATOGRAPHIC PEAKS

BACKGROUND OF THE INVENTION

The present invention relates to chromatography, and, more particularly to a system, program and method for estimating component spectra of a chromatogram with overlapping component peaks.

Analytic chemistry has provided scientists the ability to break down chemical systems into their constituents, the properties of which can then be investigated individually. Chromatography contributes to this ability by permitting scientists to determine the identity and relative concentrations of compounds in a mixture. The mixture itself can be the result of the breakdown of a highly complex molecular structure, such as a protein, so that chromatography can be used as a sub-procedure in the study of complex molecules.

Chromatography involves the flow of a mobile phase over a stationary phase. Each component of a mixture is distributed between these two phase according to a characteristic ratio. As the mobile phase moves past the stationary phase, repeated adsorption and desorption of a component occurs at a rate determined chiefly by its ratio of distribution between the two phases. To the extent that their distribution ratios are different, the components of the mixture move at different rates.

Where the distribution ratios are sufficiently different, the components of the mixture can be resolved into a series of bands. Spectral distributions can then be determined for the individual bands. A spectral distribution can be one of several types, generally corresponding to the specific chromatographic technique applied. For example, in a liquid chromatography system, in which a mobile liquid phase is passed through a stationary solid or liquid phase, a diode array detector can be used to determine the visible light or ultra-violet absorption spectra of the eluting components. Alternatively, gas chromatography systems, in which a mobile gas phase passes a stationary solid or liquid phase, can use Fourier transform infrared spectroscopy or mass spectroscopy to obtain chromatograms.

Where the mixture components are sufficiently resolved, the spectra measured as a chromatographic peak is eluting are those characteristic of a single component. However, with complex mixtures, there is some overlap of pure component spectra.

The spectra constituting an overlap can sometimes be deconvolved, i.e., mathematically estimated. Where deconvolution is possible, it is often more effective and efficient than successive chromatographic runs which might also be used, in effect, to resolve overlapping peaks.

The method of mathematical deconvolution derives from the work of Lawton and Sylvestre, *Technometrics*, Vol. 13, pp. 617-633 (1971). They showed that the spectra of mixtures of two compounds, when the spectra were normalized so that the sum of the elements in each spectrum is unity, can be represented by points in an abstract two-dimensional space that lie in a straight line. The type of normalization employed, herein referred to as "area normalization", has the effect of normalizing the spectra to unit area.

The preferred way to determine the coordinate vectors of this space was by principal component analysis of the spectra of the mixtures. Lawton and Sylvestre pointed out that estimates of the spectra of the pure compounds in the mixtures could be found from this line in the following way: if each real spectrum correspond to a point on the line, and also each point on the line corresponded to a spectrum, one could extend the line in each direction until points were reached where one or more elements of the corresponidng spectra were just less than zero. The point corresponding to the spectra of the pure compounds would lie somewhere between these end points and the nearest points corresponding to the measured spectrum of a mixture.

These methods were applied to chromatography to obtain the spectra of the components and resolve mathematically unresolved chromatographic peaks where only two components were present. See: Donald Macnaughton, Jr., L. B. Rogers, and Grant Wernimont, *Analytical Chemistry*, Vol. 44, pp 1421-1427 (1972); and Muhammed Abdallah Sharif and Bruce R. Kowalski, *Analytical Chemistry*, Vol. 54, pp. 1291-1296 (1982); Muhammed Addalah Sharif and Bruce R. Kowalski, *Analytical Chemistry*, Vol. 53, pp 518-522 (1981); and David W. Oston and Bruce R. Kowalski, Analytical *Chemistry*, Vol. 56, pp. 991-995 (1984). Borgen and Kowalski extended the method to three overlapped peaks. See Odd S. Borgen and Bruce R. Kowalski, Analytica *Chimica Acta*, Vol. 174, pp. 1-26 (1985). In this case the points corresponding to the spectra of the eluting mixtures lie on a plane in the space defined by the three principal components of the spectra of the mixtures. Here, the emphasis is on setting bounds within which the points that represent the spectra of the pure components must lie. No attempt is made to use the results of computing the concentrations to improve the estimates of the spectra.

Similar methods have been developed in which the normalization of the spectra is such that the sum of the squares of the elements of each spectrum is unity. See: Jie-Hsung Chen and Lian-Pin Hwang, *Analytical Chimica Acta*, Vol. 133, pp, 271-281 (1981); and Bernard Vandginste, Raymond Essers, Theo Bormon, Joost Reijnen, and Gerrit Kateman, *Analytical Chemistry*, vol. 57, pp. 971-985 (1985). In methods using this form of normalization, referred to as "Euclidean normalization" herein, the points corresponding to spectra in the space of three principal components lie on the surface of a sphere. The polar and azimuthal angles of the points are then used as polar coordinates in a plane, to map the points from the spherical surface to a plane, with the polar angle used as the radius vector and the azimuthal angle as the vectorial angle.

In this polar representation, it is not possible to extrapolate linearly the loci of points representing mixtures of two compounds as is done in the method developed by Lawton et al. (op.cit). Instead, various constraints are used to define the locations of the points on the plane that correspond to the best estimates of the spectra of the pure compounds partially separated chromatographically. One of the constraints used is that no spectral element be negative, and at least one be zero.

Vandeginste et al. (op. cit) used the spectral estimates to compute elution profiles for the individual compounds. They were able to improve the spectral estimates by adjusting the spectra so that the amplitudes of any two components are zero at the peak of the elution profile of the third, where the peaks are found using the first estimates. Of course, this assumption may not be appropriate.

One can also regard the data array from the chromatographic detector not as a series of spectra, but as an array of elution profiles, each one measuring the response vs. time of the signal at a specific wavelength for LC, or a specific mass number of MS. The principal components of the elution profiles can then be found.

Vandeginste et al. (op cit) used this expansion in a way completely analogous to the method using principal components of the spectra. The application of their constraints to obtain estimates of the elution profiles of the compounds works better in some cases than in the analogous case of estimating their spectra. Spectral estimates can then be obtained from the data array of spectra vs. time, using the estimated elution profiles.

A method called iterative target transform factor analysis in which an estimate of the elution profile of each compound is expanded in terms of the elution profile principal components has been developed. See: Bernard G. M. Vandginste, Wilbert Derks, and Gerrit Kateman, *Analytic Chemica Acta,* Vol. 173, pp. 253- 264 (1985); and Paul J. Gemperline, *J. Chem. Inf. Comput. Sci.,* Vol. 24, pp. 206-212 (1984). The elution profile so expanded may show negative amplitudes or secondary maxima. A new estimate of the elution profile is then made modifying the expansion to eliminate the presumably erroneous features, and the new estimate is expanded as before. When the estimate and its expansion are essentially identical, the iteration is terminated, and spectra corresponding to the elution profiles are computed by multicomponent analysis.

Harris and coworkers have developed yet another method for attacking the problem of mathematically deconvolving overlapped chromatographic bands as disclosed in U.S. Pat. No. 4,353,242. The peak shapes of the chromatographic bands are assumed to be known, and parameters of the bands such as mean position and peak width are computed from the array of data by a least squares fitting procedure. The spectra can then be computed from the data array and the elution profiles.

The foregoing and other references can be roughly summarized as follows. Deconvolution can be applied straightforwardly under each of the following conditions: (1) the spectral distributions of the components are known, for example, where only the relative concentrations of the components are unknown; and (2) at most two peaks overlap. More complex overlapping can be handled in a relatively straightforward manner by imposing certain assumptions on more complex spectral distributions. For example, one can assume that the unknown spectral distributions have a predetermined shape. Such an assumption can facilitate component estimation when correct. On the other hand, the imposition of strong assumptions can decrease the likelihood estimates obtained are valid, thus limiting confidence in the results of such methods.

Methods powerful enough to deconvolve up to three overlapping component peaks while imposing at most weak assumption on peak shape can be roughly categorized according to the type of normalization applied, i.e., there are area normalization methods and Euclidean normalization methods.

Area normalization methods permit a representation of chromatographic data in a plane in which binary mixtures of varying relative concentrations lie along a line segment defined by endpoints representing the pure component spectra of the pure compounds in the mixture. This permits straightforward linear extrapolation of pure component spectra as follows. Given a chromatographic elution sequence of compound A alone, A mixed with comppound B, B mixed with A and compound C, B mixed with C, and C alone, the pure component spectra for B corresponds to the intersection of straight line segments defined during binary mixture elutions A with B and B with C. This reliable method for extrapolating pure component spectra can serve as the basis for determining the concentration profiles for each eluting compound represented in a chromatogram.

There are two fundamental disadvantages to area normalization. The first is that it amplifies low signal regions of a chromatogram relative to large signal regions, thus amplifying noise relative to signal. The second is that area normalization permits division by zero and near-zero amounts when both positive and negative spectral components are involved, skewing any possible interpretation of results with large values of little validity.

While the second problem is not likely to be significant using raw chromatographic data, in which case all spectra data can be assumed postive, there are many situations in which negative values can be expected to occur. It is often advantageous to modify the spectra so that the sum of elements is zero, or very small. For example, one might correct for a constant offset of unknown amplitude of every element of a spectrum by requiring the average of the elements to be zero. Other commonly used modifications of spectra involve the use of the first or higher derivatives of the spectra instead of the spectra themselves. Since the sum of the elements of these modified spectra may be very small, these modifications are inconsistent with area normalization which forces the sum to be unity.

In Euclidean methods, it is the sum of the squares of the elements of each spectra, rather than the sum of the elements, that are set to unity. In comparison to area normalization, strong signal areas are emphasized over the relatively noisy weak signal areas. The terms of a sum of squares do not offset each other, so there is no special difficulty dealing with data which assumes both positive and negative values. Hence, Euclidean normalization is compatible with methods applying baseline correction or using derivatives of the spectra.

However, the polar coordinate reference frame generated using Euclidean normalization does not permit linear extrapolation of pure component spectra. Accordingly, the foregoing methods in the Euclidean category have had one or more of the following disadvantages: (1) a requirement for assumptions as to peak shape; (2) a difficulty in determining a confidence level or error bound for the result obtained; (3) inaccuracy of the results; and (4) severe computational requirements.

In addition, some Euclidean approaches impose assumptions of non-negativity to the chormatographic spectra. Such approaches are not compatible with certain baseline correction techniques that may be applied to the chromatogram before analysis, such as those yielding negative absorption cusps.

As indicated, available methods for deconvolving chromatograms in which up to three unknown spectral components overlap are limited in several ways, including accuracy and computational efficiency. Also, in most cases, no measure is provided for the errors in the estimates obtained.

Accordingly, it is an objective of the present invention to provide an improved system, program and method for deconvolving chromatograms with up to three unknown overlapping spectral components. The improvement subsists partly in an improved combination of computational efficiency and accuracy. In addition, an error bound on the estimates is provided.

SUMMARY OF THE INVENTION

In accordance with the present invention, the application of an appropriate coordinate transformation allows linear extrapolation to be used with Euclidean normalization. The novel Euclidean-extrapolation method combines the advantages of prior Euclidean and area normalization methods. Spectra expressed as Euclidean normalized linear combinations of principal factors are mapped onto a plane so that mixtures of two spectral components lie on straight lines, the endpoints of which represent the spectra of the individual components. Initial estimates of the component spectra can then be obtained by extrapolation. Error analysis can then be applied to supply an error bound on the estimate and to provide improved estimates.

Initially, an interval of interest is selected from a chromatogram. An interval of a chromatogram is itself a chromatogram. Preferably, the interval is selected so that the ends of the interval are dominated by respective single component spectra. For example, an interval might include a peak and relative minimums to either side of the peak. The data within the interval is then converted to Euclidean-normalized linear combinations of three principle factors obtained through factor analysis of the data.

Geometrically, the converted data are confined to the surface of a unit sphere. Thus, the converted data can be reexpressed in spherical coordinates $\theta$, a polar angle, and $\phi$, an azimuthal angle about an equator. This spherical representation of the data can be mapped to a plane by means of the transformation $X = \tan\theta\cos\phi$, $Y = \tan\theta\sin\phi$. This maps a typical series of spectra data to a curve with alternating straight-line segments and more or less rounded vertices, the curve lying in a "principal factor" plane.

In this principal factor plane, mixtures of two component spectra lie on a straight line segment defined by the points representing the individual spectral components. Thus, extrapolation of straight line segments representing two binary mixtures with a common component can yield an intersection representing the spectrum of that common component. Accordingly, extrapolation can be used to determine the spectra distribution of all components between the first and last in the interval.

Where more than three components appear, more accurate estimates can be obtained by analyzing each rounded vertex in the plane of the principal factors in the context of a spectra curve segment including only three vertices, the selected vertex and those immediately preceding and following it. For each curve segment, the corresponding sub-interval is factor analyzed, converted to planar coordinates as above so that the selected vertex can be extrapolated to yield an estimate for the corresponding component.

The end components of each spectra curve segment are determined by selecting a best point in the original planar expression, and the above procedure is replicated for each intermediate vertex to obtain estimations for all the components of the interval of interest. The estimates can be used to identify the associated compounds. The distribution of each component spectrum can be integrated over the interval to determine the relative concentrations of each compound in the original mixture.

Errors in the estimated component spectra can be assessed by evaluating the matrix of concentrations C, whose rows are the computed elution profiles for the components, and whose columsn are the computed concentrations found from each experimental spectrum. All negative values and all values beyond a predetermined number of standard deviations from the corresponding peak are set to zero and the remaining values are scaled so that the sum of the elements in each columns is retained. The difference between the original matrix and this revised matrix is an estimated error matrix, which can be used to determine the error in the estimated component spectra.

This error in the estimated component spectra can be used to derive revised estimated component spectra, and the error estimation can be reiterated until satisfactory convergence is achieved. The remaining error is a component in the total error. This can be combined with estimated noise and the norm of the difference between the total signal chromatogram and the reconstructed total signal chromatogram so that a total error bound can be constructed using known techniques.

The invention combines the use of Euclidean normalization of the mixture spectra with the representation of these spectra as points on a plane where the points representing mixtures of two compounds lie on a straight line. A straight line permits linear extrapolation, useful for making estimates of the spectra of pure compounds.

Euclidean normalization is preferable to normalization where the sum of elements in a spectrum is required to be unity, because it is often advantageous to modify the spectra so that the sum of elements is zero, or very small. For example, one might correct for a constant offset of unknown amplitude of every element of a spectrum by requiring the average of the elements to be zero. Other commonly used modifications of spectra involve the use of the first or higher derivatives of the spectra instead of the spectra themselves. Since the sum of the elements of these modified spectra may be very small, these modifications are inconsistent with normalization so that the sum is unity.

Further, the invention permits results to be achieved relatively quickly while using all the data available. In the iterative target transfer factor analysis method discussed in the background section above, one must find the principal factors of much larger data arrays than is called for by the present invention. The time required to compute the principal factors increases rapidly with the size of the array.

Additionally, no strong assumptions about peak shapes are made. Therefore information can be obtained from the peak shapes that are found. Other features and advantages of the present invention are apparent from the description below with reference to the following drawings.

BRIEF DESCRIPTION OF THE DRAWINGS

FIG. 6B is a graphic representation of the spectrum of the second component of FIG. 5 well-isolated chromatographically.

FIG. 8 is a reconstruction of a gas chromatography and mass spectroscopy chromatogram shown with component distributions determined using the chromatographic expression of FIG. 7.

FIG. 9 is an improved reconstruction of the chromatogram of FIG. 8 obtained in accordance with the present invention.

FIG. 10 is a table showing changes in peak areas and error bound with iteration of a routine to improve spectral estimates in accordance with the present invention.

DESCRIPTION OF THE PREFERRED EMBODIMENTS

Figure 1:
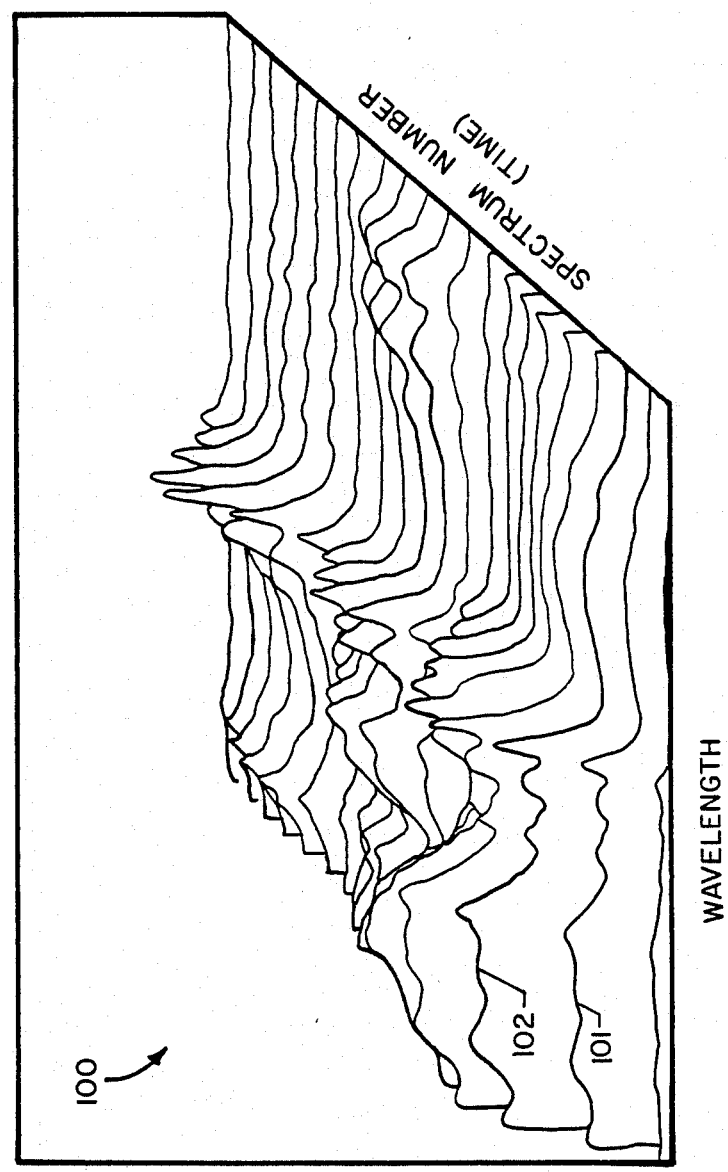
FIG. 1 is a graphic representation of ultraviolet and visible light chromatographic data showing absorbance as a function of wavelength and time.
Figure 2:
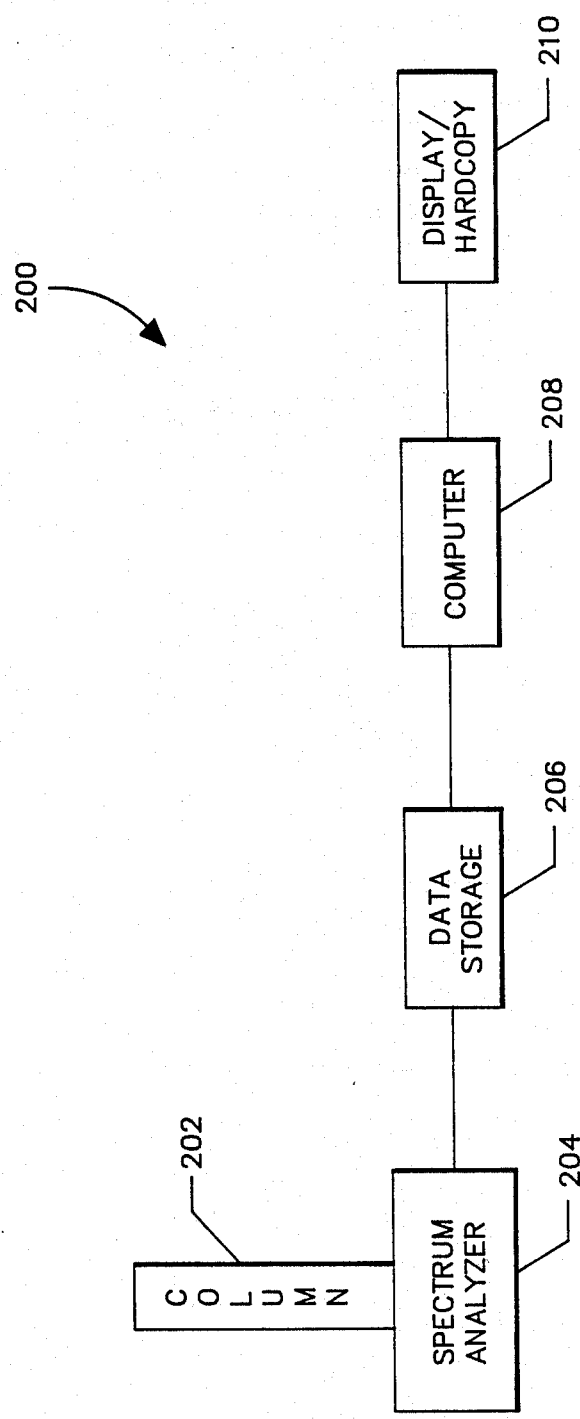
FIG. 2 is a schematic illustration of a system for obtaining and analyzing chromatographic data in accordance with the present invention.
Figure 3:
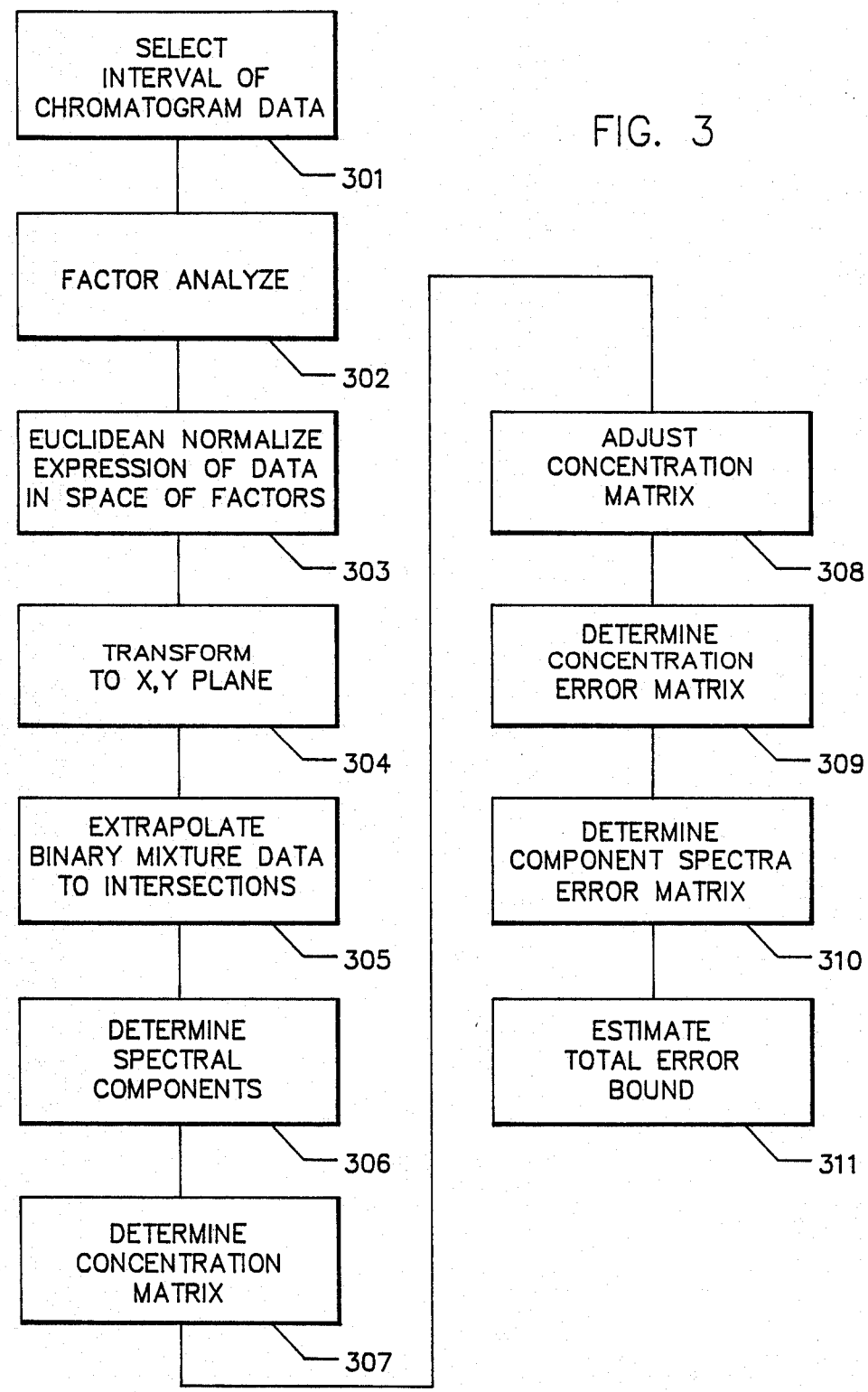
FIG. 3 is a flow chart of a method of analyzing chromatographic data in accordance with the present invention.

In accordance with the present invention, an improved system, program and method for estimating the spectra and relative concentrations of components of a mixture involves obtaining a chromatogram 100, illustrated in FIG. 1, and processing the data by means of a system 200 of FIG. 2 according to a program and method as presented in the flow chart of FIG. 3. The program is designed to deconvolve chromatographic peaks with up to three overlapping spectra components, provided each region of triple overlap to be deconvolved is immediately preceded and followed by a region in which two spectral components overlap. In addition to permitting estimates of overlapping spectral components, and their associated relative concentrations in the original mixture, the program provides for iterative improvements in the estimates and for an estimated error bound for the estimates.

The chromatogram of FIG. 1 comprises a series of spectra 101, 102, etc. Each spectrum comprises a series of intensities taken over different frequencies, $f_1, f_2, \ldots f_n$. In other words, each spectrum represents a point in frequency space with the coordinates $(f_1, f_2, \ldots f_n)$. The $i^{th}$ spectrum can thus be characterized as a vector $S(i)$ with the foregoing coordinates as its elements. Corresponding, a chromatogram, and any interval of a chromatogram can be expressed as a matrix S having a series of vectors $S(i)$ as its columns.

The illustrated chromatogram 100 is only a small section of a chromatogram with up to 100 or more peaks, and with 10–30 spectra per peak. The spectra represent ultra-violet and visible light absorption spectra taken during the elution of a chromatographic sample mixture from a chromatography column 202, of FIG. 2. The spectra are obtained by the ultra-violet and visible light spectrum analyzer 204. The spectra are analyzed by a computer 206 and a display/hardcopy device provides for display of the results, as indicated in subsequent figures.

The chromatographic data are in the form of absorption versus frequency versus time. In a subsequently described application of the invention, the results of the program are applied to data obtained through mass spectroscopy of compounds obtained through gas chromatography so that the data is in the form of quantity versus mass versus time. Of course, the computer program is not concerned with the physical referents of the data it processes. Hence, the present invention can be applied to deconvolve other types of data, provided the underlying assumptions discussed below are substantially met.

The method of the present invention requires the selection of an appropriate candidate for deconvolution, as indicated at 301 in FIG. 3. In general, the program is applied to a time interval of the chromatogram. Deconvolution is not a substitute for good chromatography. A typical chromatogram for a complex mixture can have 20–100 peaks. Most of these peaks should represent single components. However, visual inspection or a relatively efficient mathematical procedure, such as a peak purity teast, can be used to identify convoluted peaks. In addition, peaks of special interest in a mixture can be tested through deconvolution to determine whether or not multiple components are represented.

The present method involves extrapolation of component spectra from data representing preceding and succeeding component spectra. While the extrapolation can be applied readily to intermediate components, it is difficult to extrapolate the spectral components of the first and last components represented in an interval. Therefore, the interval is preferably selected so that the first and last components are accurately represented by unextrapolated data. This is best ensured by selecting an interval including amplitudes at relatively low, e.g., background levels, to either side of the peak.

The objective of the present method is to determine the "pure" spectra $P(k)$ and the elution profiles $C(i)$ of the compounds eluting during the interval. The pure spectra vectors $P(k)$ define the columns of a pure component spectra matrix P and the elution profile vectors $C(i)$ define the rows of a concentration matrix C. The spectral data, the pure spectra and the concentration matrices are related by the equation $S=PC$.

The vectors $S(i)$ are factor analyzed to determine three principal factors, as indicted at 302. The factor analysis can be simplified by grouping the data. The division into groups is done in such a way that the number of groups is maximized, up to 12, consistent with minimizing the number of spectra left over at the beginning and end of the series. The vectors within each group are added to define 10 to 12 vectors $S_r(j)$, the columns of a "reduced" data matrix $S_r$ to be factor analyzed.

For example, in an interval with 38 spectra, vectors $S(2)$, $S(3)$ and $S(4)$ are added to define a single vector $S_r(1)$. Successive combinations vectors $S_r(2)$ through $S_r(12)$ are similarly defined for succeeding groups of three $S(i)$ vectors. Vectors $S_r(1)$ through $S_r(12)$ are the columns of the matrix $S_r$ to be factor analyzed. $S(1)$ and $S(38)$ are not used in determining the principals factors.

The combinations of the $S(i)$ vectors in defining the $S_r$ matrix reduces noise and computation time, while making use of substantially all the data. This treatment does not seriously impair finding the principal components as long as the span of each group of spectra is no greater than the width of a chromatographic peak. The experimental spectra can be windowed or weighted, but they are not normalized.

A square covariance matrix Z is formed by multiplying $S_r$ by its transpose $S_r'$, i.e., $Z=S_r'S_r$. The eigenvectors and eigenvalues of Z are found by solving the equation $ZQ=QR$, where Q is a square matrix whose columns are the eigenvectors of Z and R is a diagonal matrix whose elements are the eigenvalues. Both Z and R are arranged in the order of the magnitude of the eigenvalues.

A matrix of factors $F_r$ is computed from the relation $$F_r = DQR^{-\frac{1}{2}}$$

The principal factors, or principal components, are the columns of $F_r$ corresponding to the larger eigenvalues. It is easy to show that the columns of $F_r$ are orthogonal to each other, and they consequently form an orthogonal basis that spans the same space as the columsn of $S_r$ and the experimental spectra $S(i)$.

Each spectrum $S(i)$ is then approximated by its expansion $S_f(i)$ in the space of the first three principal factors, $f_x$, $f_y$, and $f_z$ and the resulting vectors are Euclidean normalized, as indicated at 303, i.e., $$S_f(i) = \frac{(S(i) \cdot f_x)f_x + (S(i) \cdot f_y)f_y + (S(i) \cdot f_z)f_z}{[(S(i) \cdot f_x)^2 + (S(i) \cdot f_y)^2 + (S(i) \cdot f_z)^2]^{\frac{1}{2}}}$$

over all i in the selected interval. In other words, all the original data in the interval are expanded individually. The groups $S_f(j)$ are not considered after the factor analysis. In the example above, $i = 1$ through 38. The expansion can be re-expressed in terms of coefficients of expansion $$S_f(i) = S_x(i)f_x + S_y(i)f_y + S_z(i)f_z$$

Due to the Euclidean normalization, the sum of the squares of the coefficients of each spectrum in the space of the three principal factors in unity. Geometrically, this means that all spectra within the interval are represented as points on a unit sphere. Furthermore, linear combinations of two spectra lie on an arc of a great circle on the unit sphere. Thus, all possible binary mixtures lie on a great arc having the spectra of single compounds at its endpoints.

Since all spectral data lie on the unit sphere, they can be expressed in polar coordinates $\theta$ and $\phi$ where $\theta$ is the polar angle and $\phi$ is the azimuthal angle.

$$\theta(i) = \cos^{-1}\left[\frac{S_z(i)}{[(S_x(i))^2 + (S_y(i))^2]^{\frac{1}{2}}}\right]$$

$$\phi(i) = \tan^{-1}\left[\frac{S_y(i)}{S_x(i)}\right]$$

This spherical surface space can be mapped, as indicated at 304, into a X,Y plane W by the following transformation:

$$W_x = \tan(\theta)\cos(\phi)$$

$W_y = \tan(\theta)\sin(\phi)$ The original spectral data S are now expressed as points on the plane W, i.e., $S_w = S_x W_x + S_y W_y$.

Figure 4:
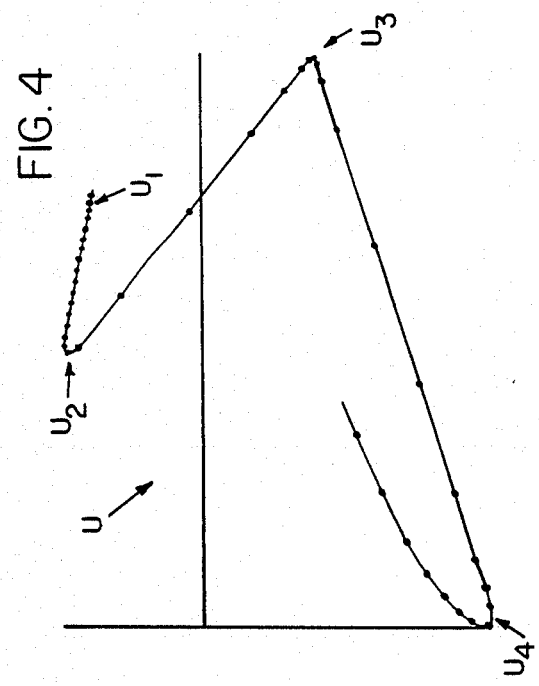
FIG. 4 is a graphic representation of the ultra-violet and visible light spectra of liquid chromatography data expressed in a plane of three principal factors.

This transformation not only maps the surface of the unit sphere into the plane W, but also maps great circles into straight lines and great arcs into straight line segments. Thus, in the palne W, binary mixtures of two compounds lie on a straight line segment with the spectra of the two compounds defining the endpoints of the segment. Theoretically, a chromatographic interval characterized by alternating unitary and binary subintervals would be represented by a series of straight line segments joined by vertices $V(k)$ representing the spectra of the pure compounds.

Where the chromatographic interval includes at least one sub-interval with mixtures of three components bounded by sub-intervals with binary mixtures, a rounded, rather than a sharply defined, vertex $U(k)$ is formed in the spectra curve, as typified by rounded vertices $U_1$, $U_2$, $U_3$ and $U_4$ in FIG. 4. A rounded vertex $U(k)$ can be used to indicate the region of the virtual vertex $V(k)$ corresponding to the spectrum for a single compound; the precise location of the vertex $V(k)$ representative of the pure component spectra $P(k)$ in the plane W being identified through extrapolation, indicated at 305 in FIG. 3.

Before detailing the preferred approach to extrapolation, it is instructive to note the analogy between the present representation of the spectral data and that afforded using the extrapolation approach based on area normalization instead of Euclidean normalization. The geometric correspondence between the curves generated by the two deconvolution approaches implies that the same methods of linear extrapolation to obtain spectral distributions and relative concentrations can be applied. However, the spectral data as represented in the respective planes do not correspond due to the different normalizations applied.

As indicated in the background section above, a major advantage of Euclidean normalization methods over methods employing area normalization is that the former is less sensitive to noise and more compatible with various baseline correction techniques and various approaches to data modification which can include negative spectral values. Thus, the present invention provides the advantages of linear expolation obtained by prior are normalization methods, without the disadvantages inherent in area normalization.

Returning to the method of the present invention, the sequence of points corresponding to the chromatogram lies along a curve U in the constructed X,Y plane W. Ideally, at least, this curve U would consist of straight line segments with more or less sharp curved segments joining them.

The curve U is subdivided for further analysis using the vertices $U(k)$ as reference points. In the limit of low noise, the number of vertices $U(k)$, in the chromatogram curve in the plane W is equal to the number of components represented in the series of spectra $S(i)$. Noise displaces the spectral points from the location they would otherwise have and, as might be expected, can make determining the number and position of vertices $U(k)$ difficult.

The preferred algorithm for locating vertices consists of finding the maxima in the correlation between each spectrum $S_w(i)$ and the next $S_w(i+1)$. If the maxima are too close to each other, they are presumed to represent a single rounded vertex, which is taken to be to the point midway between.

Where there are more than three vertices, better spectral estimates can be obtained by performing each extrapolation in the space best suited for the vertex to be determined. Accordingly, if there are more than three vertices, overlapping series of data are defined by points midway between vertices in such a way that each group has three components in it. Each group is then further analyzed to determine the spectral component corresponding to the intermediate vertex by extrapolation. The number of groups is thus equal to the number of vertices minus two, specifically, the first and last vertices.

Given the curve U with four vertices $U_1$, $U_2$, $U_3$, and $U_4$ a point midway between $U_3$ and $U_4$ cooperates with the first spectrum S(1) of the interval to define a first group including $U_1$, $U_2$ and $U_3$, but excluding $U_4$. This first group is used for the extrapolation of the spectral component most closely associated with vertex $U_2$. Similarly, a point midway between $U_1$ and $U_2$ cooperates with the last spectrum of the interval to define a second group including $U_2$, $U_3$ and $U_4$, but excluding $U_1$. This second group is used for the extrapolation of the spectral component most closely associated with vertex $U_3$.

The extrapolation technique is not applicable to the first and last vertices of the chromatogram curve. Thus, the first and last vertices located by finding the correlation maxima are the initial estimates for the first and last component spectra represented in the interval. These estimates should be valid to the extent that the first and last vertices represent single compounds rather than mixtures. This condition is generally satisfied by defining the ends of the interval of interest away from the peaks. In the example, the spectra corresponding to $U_1$ and $U_4$ are taken to represent the spectra of the first and fourth compounds to be eluted during the selected interval.

The vectors S(i) representing each group are factor analyzed using the algorithm originally applied to the entire interval. Thus, the $i^{th}$ group has associated with it a matrix $F_i$ of three principal factors, $F_{ix}$, $F_{iy}$, and $F_{iz}$. For each group, the vectors S(i) are expanded in the space defined by these factors, and the expansion is Euclidean normalized. Thus, each portion of the curve has associated with it a space defined by a matrix $F_i$, of three principal factors. The data in each portion of the curve are then expanded and Euclidean normalized in the space of the corresponding principal factors. The transformation to polar and then to planar coordinates is performed as above with respect to the entire interval.

Since, in general, the matrices $F_i$ differ, the groups of data are mapped into different planes $W_i$. In effect, the present method selects the optimal plane $W_i$ for extrapolating each vertex V(k) when more than three compounds are involved. At this point, the case of more than three vertices U(k) is reduced to separately treatable instances of curves with three vertices.

As indicated above, the expansions of the spectra at the first and last vertices on plane W for the complete interval are used for the estimates of the spectra of the first and last components that elute in the interval being analyzed. In the example above, these are the first and fourth spectral components for the interval, so that V(1) = U(1) and V(4) = U(4).

Estimates for the intermediate components are found using the corresponding factor space, by extrapolating straight line segments to either side of the respective vertex, as described by O.S. Borgen and B.R. Kowalski (op. cit.). The coordinates of the intersection are the coefficients of the linear expansion of the estimated spectrum in terms of the respective set of principal components.

In the example, the vertex V(2) defined by the intersection of the straight line segments in the plane $W_1$ of the three principle factors for the first group is used to estimate the second spectral component, corresponding to curve vertex U(2). Likewise, straight line segments in the plane $W_2$ of the three principle factors for the second group are used to extrapolate V(3), the estimate the third spectral component, corresponding to vertex U(3).

The pure component spectra P(k) are given by the relation $P(k) = F_k V(k)$, where P(k) is the estimated spectrum for the $k^{th}$ compound eluted during the interval, $F_k$ is the corresponding matrix of factors, and V(k) is the vector comprising the coordinates of the $k^{th}$ extrapolated vertex. In the example, the spectrum P(2) of the second component eluting during the interval is equal to the product of the corresponding factor matrix $F_2$ and the coordinates of the extrapolated intersection V(2) by curve vertex U(2). The estimates of the spectra of the component compounds that have been made as described above comprise a matrix P, whose columns are the pure component spectra P(k), completing the method step indicated at 306 of FIG. 3.

The concentrations relative to the concentrations of each compound for which the sum of the squares of the spectral elements is unity one are found, as indicated at 307 of FIG. 3, by least-squares fitting of the estimated spectra P(k) of the component compounds to each experimental spectrum and then integrating over the interval, for example by using the trapezoidal rule, to find their total area.

The least squares solution to the equation

S(i) = PC(i) is that which minimizes the Euclidean norm $\|S(i) - PC(i)\|$, where S(i) is the experimental spectrum to be fitted by the spectra that are the columns of the matrix P, and C(i) is the corresponding vector of relative concentrations. The number of elements in vector C(i) is equal to the number of components, and each element corresponds to the relative concentration of the respective component eluting as P is determined.

There are a variety of techniques for minimizing such a Euclidean norm. An orthogonalization method in which Householder transformations change S into an upper triangular matrix is preferred because it is efficient and has very good numerical stability. In the initial solution, the series of experimental spectra S(i) is segmented into overlapping groups with three component peaks each, in a way similar to that used for factor analysis in connection with estimating the spectra. The matrix P of the pure component spectra is then limited to three columns containing the estimated spectra of the compounds present in that interval. This procedure improves the overall fit.

Figure 6A:
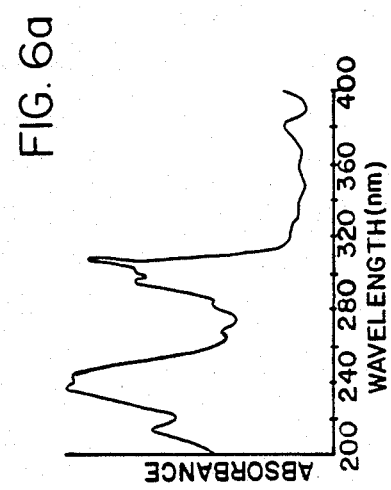
FIG. 6A is a graphic representation of the spectrum of the second component of FIG. 5 as determined in accordance with the present invention.
Figure 5:
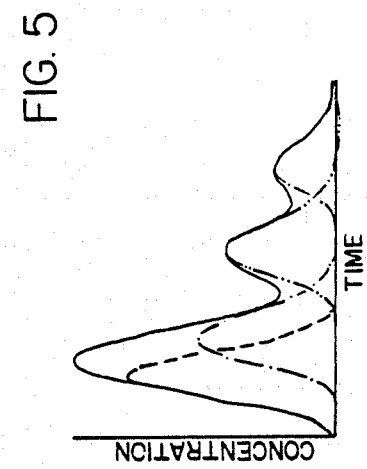
FIG. 5 is a reconstruction of an ultra-violet and visible light chromatogram shown with component distributions determined using the chromatographic expression of FIG. 4.

The concentration vectors C(i) can be used to obtain a concentration versus time plot for each of the four principle components P(k) as illustrated in FIG. 5. A curve P representing the sum of the four components P(k) serves as a reconstruction of the original data matrix S. The effectiveness of the present method is demonstrated by comparing the estimated spectrum for the second compound corresponding to P(2) as illustrated in FIG. 6A with the experimental spectrum in FIG. 6B of the same compound well-separated chromatographically.

The program provides for improving the original estimates, as indicated in the second column of FIG. 3, by comparing the computed concentrations with a standard. In improving the original estimates, it is convenient to express the original spectra in a space defined by a principal factor matrix G, where the number of principal factors is set equal to the number of compounds present.

The factor matrix G is determined by factor analyzing all the experimental spectra S(j) between the first and last vertices, e.g., between U(1) and U(4) in the example. In general, the range of j is truncated with respect to the range of index i for the entire experimental interval. In the example, j = 3,4,... 33. Once G is obtained, the full set of spectra data S is used in the analysis. The expansion of the truncated data in the space of matrix G is denoted as $S_g$; likewise the expansion of S(i) in the space G is denoted $S_g(i)$.

Then, $S_g = G'S = G'PC_1 = A_1C_1$ $S_g(i) = G40\ S(i) = G'PC_1(i) = A_1C_1(i)$ where $S_g(i)$ is the expansion of the $i^{th}$ spectrum in the space of factors defined by matrix G, G' is the transpose of G, and $A_1$ is a component factor matrix as defined by $A_1 = G'P$. The component factor matrix $A_1$ is a (k x k, e.g. 4 x 4, in the example) square matrix, the columns of which are vectors whose elements are equal in number to the compunds present. $C_1(i)$ is the concentration vector for S(i) having the relative concentrations of the compounds as its elements. The subscript "1" denotes that $A_1$ and $C_1(i)$ are the first estimates used in an iterative procedure for determining successively improved estimates. The elements of $C_1(i)$ can be found by solving the equation $S_g(i) = A_1C_1(i)$ using the same algorithm used above to solve the least squares.

The rows of matrix $C_1$ are the computed elution profiles for the components; the columns of $C_1$ are the computed concentrations found from each experimental spectrum. An error matrix E is obtained from $C_1$ as follows. All negative values of the concentrations are set to zero. The standard deviations of the concentration profiles are computed. In addition, all values are predetermined number of standard deviations, e.g., three, from the means of the concentration profiles are set to zero. The remaining concentrations are renormalized to restore the original sum of the elements for each column yielding, in correspondence with step 308 of FIG. 3, an adjusted concentration matrix D, i.e., $\Sigma_k C_1(i,k) = \Sigma_k D(i,k)$. Note that iterative subscripts are implied in the derived concentration matrix and the error matrices below.

Matrix subtraction yields a concentration error matrix $E = C_1 - D$, as indicated at 309. A corresponding spectral component error matrix B, as required at 310, can be computed from the relation $S_g = A_1C$ by explicitly including error terms in the expression as follows: Using the approximation $S_g = A_1C_1$, this reduces to $0 = (A_1 + B)E + BC_1$ which can be solved for an estimate of B.

The estimate of B can be used to obtain an improved estimate for the matrix of pure component spectra:

$A_2 = A_1 - B$ An improved concentration matrix can then be obtained by solving $S_g = A_2C_2$ By incrementing the indices and iterating the above procedures, new values of E and B can be computed, leading to generally better values for A and C. The improved values of the component spectra can be made explicit by the relation $A = GP$.

Generally, with iteration, the value of B becomes smaller. It does not necessarily go to zero, since the referent of interest may not be attainable with a limited number of factors. When the iteration process seems to work well, the change in spectral estimates is relatively slight. At each stage of the iteration process, B provides for an estimate of the error in the component spectra.

The error in the estimated component spectra is one of two sources of error in the computation of concentration. The other source of error is noise in the experimental spectra. By assuming that the noise is orthogonal to the principal factors, its root means square amplitude is given by the Euclidean norm $\|S(i) - GG'S(i)\|$. Because of the factor expansion we are using, this is also equal to the norm of the residual misfit between the experimental spectrum and the least-squares linear combination of estimated component spectrum.

A total error bound can be computed using the estimates for the two types of error in the computation of concentration, as indicated at 311. Since A is a square matrix, the important quantity in estimating the error bound is the least upper bound of its inverse, lub-$(A^{-1}) = 80_n^{-\frac{1}{2}}$, where $\lambda_n$ is the smallest characteristic value of A'A. The norm for the total noise can be estimated by $\|\Delta Y\| = \|\Sigma(S(i) - GG'S(i)\|$ The norm for the total concentration vectors can be estimated by $\|X\| = \|\Sigma C(i)\|$ The error bound, $\|\Delta X\|$, is estimated using a method adapted from J. Stoer and R. Bulirsch, *Introduction to Numerical Analysis*, Springer-Verlag, New York, 1980.

$$\|\Delta X\| = lub(A^{-1})\ lub(B)\ \|X\| + (lub(A^{-1}))^2\ lub(B)\ \|\Delta Y\| + lub(A^{-1})\ \|\Delta Y\|$$

It should be emphasized that the error bound is only an estimate, primarily because we can only estimate B, and lub(B) is not precisely the same thing as the least upper bound of the errors in the matrix of component spectra.

An additional quantity is also evaluated: the norm of the difference between the total signal chromatogram and the reconstructed total signal chromatogram:

$$(\Sigma(\Sigma S_{ij} - \Sigma P_{ik}C_{kj}))^2)^{\frac{1}{2}}$$

Since the spectra are formed from linear combinations of the principal factors, the sum of the relative concentrations should agree very well with the total relative concentrations. Therefore this difference is generally a relatively small number, contributing insignificantly to an estimated total error bound.

While the shape of the peaks is an important diagnostic tool for deciding whether the answers produced are to be believed, the peaks may look all right, and yet there can be considerable error. A large value for lub-$(A^{-1})$ will indicate that this may be the case.

If lub$(A^{-1})$ is large, as it will be if component spectra are highly concentrated, the error bound may very well be larger than the integrated area of a component peak, especially if the peak is small. The error in each component peak must be less than the error bound, but one cannot really say how much of the total error should be ascribed to each peak.

The error bound may not be a sufficient measure of error if a mistake is made in determining the number of compounds present or if an assumption such as linearity does not apply. In addition to the error bound, it is important to examine the deconvoluted chromatographic peaks. If the shape of the peaks is implausible, the result should be treated with extreme, if unquantifiable, caution.

The complete spectra of the components are reconstructed from the same spectra used to form the data matrix, without any weighting or windowing, by assuming that they are the same linear combination of the original data that the weighted component spectra used for deconvolution are of the weighted spectra that comprise the data matrix. When the estimates of the weighted component spectra are "improved", the complete spectra are also updated and stored.

In the case of the sample of FIGS. 4 and 5, the noise is small and the spectra estimates are good, as demonstrated by the comparison, in FIGS. 6A and 6B, of the calculated and experimental spectra for the second and least resolved components. Consequently, the procedure to improve the estimates results in barely perceptible changes.

Figure 7:
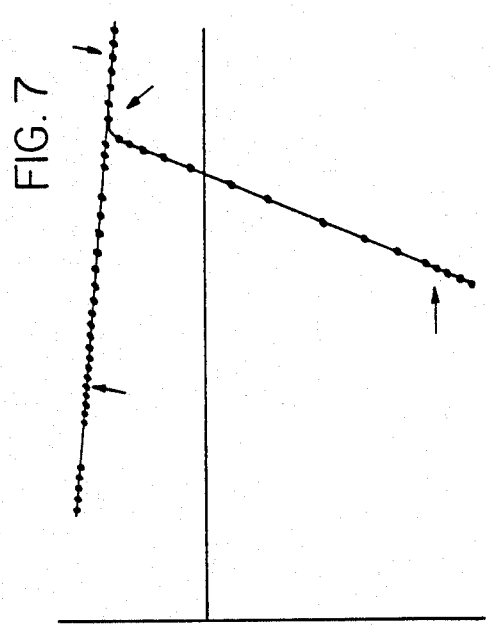
FIG. 7 is a graphic representation of gas chromatography and mas spectroscopy chromatographic data expressed in a plane of three principal factors.

The effect of the improvement procedure shows up much more strongly in the deconvolution of a section of a chromatogram obtained using gas chromatography with mass spectroscopy (GC/MS) techniques. The projections of the mass spectra in the space of the first three principal components are shown in FIG. 7 whence it can be seen that there are initial and final bunches of points and two changes in direction of the locus of points in between. This constitutes four vertices, and hence four compounds are taken to be present.

In this case, unless there is some preliminary smoothing of the data, the vertex-picking algorithm finds too many vertices because of the noise in the data. Vertices should be at regions where the density of data points in their locus plane is a maximum, corresponding to maximum in the relative concentrations of the eluting compounds. It is therefore easy to reject the extra ones that appear where the density of points is low. After rejecting the low density maxima, four rounded vertices 701, 702, 703 and 704 are identified, indicating four principal components.

In accordance with steps 301–307 in the first column of FIG. 3 leads to the deconvoluted peaks shown in FIG. 8. The negative amplitude for the second component indicates that the estimates for the spectra could be improved. The results after five iterations of the improvement procedure, steps 308–311 in the second column of FIG. 3, are shown in FIG. 9.

The iterative improvement process does not change the spectral estimates very much. As might be expected when there are only weak requirements on the elution profiles, the estimates must be reasonably accurate in the first place if the procedure is to converge to a better result. The table of FIG. 10 shows how the estimates of peak areas and error bound change with each iteration. Except for the increase in the second peak's area as the negative part disappears, changes in peak area are less than 3% after the first iteration.

In accordance with the foregoing, a system, program and method for deconvolving chromatographic peaks is presented having the following characteristics. (1) Deconvolution can be performed in a reasonable time. (2) The chromatographic overlap can be fairly complicated; i.e., up to three components may elute at once, and chains of at least six compounds are readily accommodated. (3) The method is applicable to any sort of chromatographic detector that produces spectra whose amplitudes are linear with concentration. (4) No assumptions are made about the shape of the elution peaks except, in the improvement routine, non-negativity and negligible amplitude away from the mean. (5) No assumptions whatsoever are made about the structure of the spectra of the constituent compounds. (6) An error bound is obtained on the computed concentrations. (7) No previous knowledge of the spectra of the eluting compounds is required. (8) Estimates of the full spectra of the eluting compounds are created that can be used to identify them.

These features obtain when the present invention is applied to chromatographic or analogous data. The data need not be in the form of raw spectra: the present invention can be applied to data after base-line correction has been effected, and the present invention can be applied to modified data arrays, such as result when the first or higher order derivatives of spectral data are obtained. Since there are innumerable equivalent procedures for implementing each step of the invention, its scope is limited only by the following claims.

What is claimed is:

1. A method comprising the steps of:
   obtaining a mixture including plural components;
   chromatographically processing said mixture to obtain an elution in which said components are at least partially separated chronologically;
   spectrally analyzing said elution to obtain a series of data spectra;
   constructing a chromatogram from said series of data spectra;
   factor analyzing said chromatogram so as to determine three principal factors;
   expressing each data spectrum as a Euclidean-normalized linear sum of said three principal factors so that each data spectrum can be represented as a point on the surface of a sphere with unit radius;
   performing a coordinate transformation on said data spectra, said coordinate transformation being selected to map great circles onto straight lines in a plane; and
   deriving component spectra for said components of said mixture from said data spectra as expressed in said plane.

2. The method of claim 1 further comprising a step of determining a concentration matrix which when multiplied by a matrix representing said component spectra best reconstructs the original series of spectra data.

3. The method of claim 2 further comprising a step of determining a concentration error matrix as the difference between said concentration matrix modified by setting all values representing negative concentrations to zero and all values representing concentrations a predetermined number of standard deviations from the peak of the respective component and the concentration matrix itself.

4. The method of claim 3 further comprising the step of determining a component error matrix B from the equation $(A+B)E = -BC$ where A is said concentration matrix, E is said concentration error matrix, and C is said concentration matrix.

5. The method of claim 4 further comprising the step of obtaining an improved component matrix $A_2$ from the equation $A_2 = A_1 - B$.

6. The method of claim 5 further comprising the step of obtaining an improved concentration matrix by determining the concentration matrix which best reconstructs the original chromatogram given component matrix $A_2$.

7. The method of estimating component spectra of an interval of a chromatogram, said method comprising the steps of:
selecting an interval of a chromatogram, said interval comprising a series of data arrays, each data array representing values of a dependent variable at a respective value of an independent variable;
expressing each data array as a Euclidean-normalized linear sum of the three principal factors of said chromatogram so that each data array is represented by a point on a sphere of unit radius;
expressing said data arrays as points on a plane by means of a coordinate transformation which maps great circles of a sphere onto straight lines in a plane;
determining from said planar representation of said data arrays a series of vertices, at least some of said vertices being determined through linear extrapolation; and
estimating the component spectra from the expression of said data arrays as points on a plane.

8. The method of claim 7 further comprising the step of determining a concentration matrix which best reconstructions the original chromatogram in the interval of interest given the estimated component spectra.

9. The method of claim 8 further comprising the steps of:
determining a concentration error matrix by subtracting said concentration matrix from a modified concentration matrix in which all values representing negative concentrations in said concentration matrix are set to zero and all values beyond a predetermined number of standard deviations from the peak of a respective component are set to zero;
using the concentration error matrix to derive a spectral component error matrix;
using the spectral component error matrix to obtained an improved spectral component matrix; and
using the improved spectral component matrix to determined an improved concentration matrix.

10. A system for estimating the component spectra of an interval of a chromatogram, said system comprising:
first means for obtaining a chromatogram and identifying an interval of interest thereof, said interval comprising a series of data arrays, each data array representing values of a dependent variable at a respective value of an independent variable;
second means for expressing each data array as a Euclidean-normalized linear sum of the three principal factors of said chromatogram so that each data array represents a point on a sphere of unit radius;
third means for expressing said data arrays as points on a plane by means of a coordinate transformation which maps great circles of a sphere onto straight lines in a plane; and
fourth means for determining from said planar representation of said data arrays a series of vertices, at least some of said vertices being determined through linear extrapolation; and
fifth means for estimating the component spectra from the expression of said data arrays as points on a plane.

11. A computer program comprising:
first means for factor analyzing a data matrix to determine three principal factors;
second means for expressing each data array as a Euclidean-normalized linear sum of the three principal factors of said chromatogram so that each data array represents a point on a sphere of unit radius;
third means for expressing said data arrays as points on a plane by means of a coordinate transformation which maps great circles of a sphere onto straight lines in a plane; and
fourth means for determining from said planar representation of said data arrays a series of vertices, at least some of said vertices being determined through linear extrapolation; and
fifth means for estimating the component spectra from the expression of said data arrays as points on a plane.

12. The program of claim 11 further comprising means for determining a concentration matrix which best reconstructions the original chromatogram in the interval of interest given said estimated component spectra.

13. The program of claim 12 further comprising:
means for determining a concentration error matrix by subtracting said concentration matrix from a modified concentration matrix in which all values representing negative concentrations in said concentration matrix are set to zero and all values beyond a predetermined number of standard deviations from the peak of a respective component are set to zero;
means for deriving a spectral component error matrix from said concentration error matrix;
means for determining an improved spectral component matrix from said spectral component error matrix; and
means for determining an improved concentration matrix form said improved spectral component matrix.

* * * * *

UNITED STATES PATENT AND TRADEMARK OFFICE
CERTIFICATE OF CORRECTION

PATENT NO. : 4,807,148

DATED : Feb. 21, 1989

INVENTOR(S) : Richard F. Lacey

It is certified that error appears in the above-identified patent and that said Letters Patent is hereby corrected as shown below:

Column 1, line 21, "phase" should be --phases--;
Column 2, line 2, "correspond" should be --corresponded--;
Column 2, line 20, "Analytical" should be in italics;
Column 2, line 24, "Analytica" should be in italics;
Column 2, line 34, After "such" insert --that--;
Column 2, line 36, "Analytical" should be --Analytica--;
Column 3, line 68, "comppound" should be --compound--;

Column 4, line 41, "derivatives" should be --derivates--;
Column 4, line 53, "chormatographic" should be --chromatographic--;
Column 5, line 9, "Euculidean" should be --Euclidean--;
Column 6, line 2, "columsn" should be --columns--;
Column 6, line 8, "columns" should be --column--;
Column 7, line 12, "mas" should be --mass--;
Column 7, line 51, "corresponding" should be --correspondingly--;
Column 7, line 61, After "the" insert --spectra is stored in a data storage 206 and the--; Column 7, line 62, "206" should be --208--;
Column 7, line 63, "device" should be --device 210--;
Column 8, line 57, "principals" should be --principal--;
Column 9, line 14, "columsn" should be --columns--;
Column 9, line 34, "in" should be --is--;
Column 9, line 63, "palne" should be --plane--;
Column 10, line 35, "expolation" should be --extrapolation--;
Column 10, line 36, "are" should be --area--;
Column 11, line 24, "peaks" should be --peak--;
Column 13, line 13, "G40 S(i)" should be --G'S(i)--;
Column 13, line 20, "compunds" should be --compounds--;
Column 13, line 48, After "follows:" insert $--S_g = (A_1+B)(C_1+E)$
$= (A_1+B)E+A_1C_1+BC_1--$;

Column 14, line 16, "$80_n$" should be --$\lambda_n$--;

UNITED STATES PATENT AND TRADEMARK OFFICE
CERTIFICATE OF CORRECTION

PATENT NO. : 4,807,148

DATED : Feb. 21, 1989

INVENTOR(S) : Richard F. Lacey

Page 2 of 2

It is certified that error appears in the above-identified patent and that said Letters Patent is hereby corrected as shown below:

Column 14, line 19, "GG'S(i)" should be --GG'S(i)$\|$ --;
Column 14, line 24, "$\Sigma$C(i)" should be --$\Sigma$C(i)$\|$ --;
Column 14, line 44, ")$^{2\frac{1}{2}}$" should be --)$^{\frac{1}{2}}$--;
Column 14, line 58, "concentrated" should be --correlated--;

Signed and Sealed this

Sixth Day of February, 1990

Attest:

JEFFREY M. SAMUELS

*Attesting Officer*   *Acting Commissioner of Patents and Trademarks*